US00PP12146P2

(12) United States Plant Patent
Skotak, Jr.

(10) Patent No.: US PP12,146 P2
(45) Date of Patent: Oct. 16, 2001

(54) AECHMEA PLANT NAMED 'MAYA'

(75) Inventor: Chester Skotak, Jr., Alajuela (CR)

(73) Assignee: Deroose Plants BVBA, Evergem (BE)

( * ) Notice: Subject to any disclaimer, the term of this patent is extended or adjusted under 35 U.S.C. 154(b) by 0 days.

(21) Appl. No.: 09/419,913

(22) Filed: Oct. 18, 1999

(51) Int. Cl.[7] ..... A01H 5/00
(52) U.S. Cl. ..... Plt./370
(58) Field of Search ..... Plt./370

*Primary Examiner*—Bruce R. Campell
*Assistant Examiner*—June Hwu
(74) *Attorney, Agent, or Firm*—Foley & Lardner

(57) ABSTRACT

An Aechmea plant named 'Maya' characterized by having wide, tongue-shaped leaves that are green with grey-white over lay; arched foliage which decreases from the bottom to the top of the plant; foliage that has no spines on the leaf edge; large, long lasting inflorescence which is domed-shaped and less compressed with a soft reddish-pink color; and petals which become less visible after the anthesis.

2 Drawing Sheets

BACKGROUND OF THE INVENTION

The present invention comprises a new and distinct cultivar of Aechmea plant, herinafter referred to by the cultivar name 'Maya'. The genus Aechmea is a member of the family Bromeliaceae.

Aechmea comprises a genus of more than 168 species of evergreen perennials suitable for cultivation in the home or in the greenhouse. Aechmea may be terrestrial or epiphytic. For the most part, the species vary in diameter from 12 to 18 inches to 3 or 4 feet and have rosettes of spiny-edged leaves.

Flowers and bracts of Aechmea frequently have brilliant colors and may last for several months. The range of colors for Achmea is generally from yellow through orange but may also include pink, orange, red and red-purple. Tubular, three-petalled flowers may also appear but are usually short-lived.

Aechmea may be advantageously grown as pot plants for greenhouse or home use. Typically, the plants are shaded from direct sunlight, and the central, vaselike part of the leaf rosette is normally filled with water.

Aechmea is native to tropical America. Leaves of Aechmea are usually formed as basal rosettes which are still and entire and in several vertical ranks. Aechmea has terminal spikes or panicles which are often bracted with petals united in a tube longer than the calyx.

Asexual propagation of Aechmea is frequently done through the use of tissue culture practices. Propagation can also be from offshoots which can be detached from the mother plant and grown in an appropriate soil or bark mixture. Methods for cultivating and crossing of Aechmea are well known.

The new cultivar is a product of a planned breeding program and was originated from a hybridization made during such a program in Balsa, Costa Rica in 1988. The female or seed parent was a red form of *Aechmea cuculata* (unpatented). The male or pollen parent was a spineless form of *Aechmea fasciata* (unpatented). The parental cultivars are not publicly available in the United States. 'Maya' is distinguishable from *Aechmea cuculata* by the lack of spines on its leaf edges and by its oblong elliptic floral bracts. 'Maya' is distinguishable from *Aechmea fasciata* by its bigger, but less dense inflorescence, its dome shaped inflorescence, and by the lack of spines on its leaf edges. 'Maya' was discovered and selected as a flowering plant within the progeny of the stated cross by the inventor, Chester Skotak, Jr., in 1994, in a controlled environment in a nursery in Balsa, Costa Rica.

'Maya' is characterized by its spineless leaves and tall, reddish-pink inflorescence, which keeps its color for several months. Asexual reproduction of the new cultivar by tissue culture was performed by or under the supervision of the inventor in a controlled environment in 1995, in Evergem, Belgium, and by cuttings in Balsa, Costa Rica, and has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be basic characteristic of 'Maya' which in combination distinguish this Aechmea as a new and distinct cultivar:

1. Wide, tongue-shaped leaves that are green with grey-white over lay;

2. Arched foliage which decreases from the bottom to the top of the plant;

3. Foliage that has no spines on the leaf edge;

4. Large, long lasting inflorescence which is domed-shaped and less compressed with a soft reddish-pink color; and 5. Petals which become less visible after the anthesis.

'Maya' has not been observed under all possible environmental conditions. The phenotype of the new cultivar may vary significantly when grown under different conditions of temperature, light and other determining factors without any change in genotype. The following measurements and comparisons describe 12 month old plants grown in Evergrem, Belgium under greenhouse conditions which approximate those generally used in commercial practice.

Of the many commercial cultivars known to the present inventor, the most similar in comparison to 'Maya' is the cultivar 'Friedericke' (U.S. Plant Pat. No. 5,872). 'Maya' and 'Friedericke' have a similar plant and leaf shape. However, the leaves of 'Maya' display a greater degree of arching than the leaves of 'Friedericke'. The inflorescence of 'Maya' is less compressed and shows more branches on the main stem than the inflorescence of 'Friedericke'. The basal bracts of 'Maya' cover up to one-half of the inflorescence, whereas the basal bracts of 'Friedericke' cover almost the total of the inflorescence.

BRIEF DESCRIPTION OF THE DRAWING

The accompanying photographic illustrations show a typical 'Maya' plant following growth under appropriate growing conditions, with colors being as true as possible with illustration of this type.

FIG. 1 is a side view of the inflorescence and foliage characteristics of 'Maya'.

FIG. 2 is a close-up view of the inflorescence of 'Maya'.

DETAILED BOTANICAL DESCRIPTION

The following observations, measurements and values describe plants grown in Evergem, Belgium, under greenhouse conditions which closely approximate those generally used in horticultural practice. Color references are made to The Royal Horticultural Society (R.H.S.) Color Chart, except where general colors of ordinary significance are used.

Classification:

*Commercial.*—Aechmea cv. Maya.

*Botanical.*—(*Aechmea cuculata*×*A. fasciata*) cv. Maya.

Parentage:

*Male parent.*—*Aechmea fasciata.*

*Female parent.*—*Aechmea cuculata.*

Propagation: Vegetative, by tissue culture.

Plant:

*Form.*—Funnel-form rosette.

*Height.*—Approximately 70 cm when in full bloom, including 13 cm pot and rootstock.

*Diameter.*—Approximately 65–70 cm.

*Growth habit.*—Upright.

*Vigor.*—The growing time for a commercial liner, out of a 50 cell pack, to a blooming 6 inch plant is 12 months.

Foliage:

*Shape.*—Ligulate, tongue-shaped, and strongly arching from the middle to the top. The arching decreases from the bottom to the top of the plant.

*Arrangement.*—Rosette.

*Apex.*—Mucronate.

*Size.*—Length: Approximately 45–50 cm. Width: Approximately 8.5 cm at the sheath, 6.5 cm in the middle and 2–3 cm wide at the leaf tip.

*Color.*—Sheath: Green, approximately RHS 138B, over lay with white-grey. Middle (20 cm from the leaf tip): Upper leaf surface: Green, approximately RHS 137A–B, over lay with grey, RHS 191C. Lower leaf surface: Green, RHS 146A, over lay with grey, RHS 191C.

*Margin.*—Spineless.

*Veins.*—Not visible.

*Surface texture.*—Smooth (both upper and lower surfaces).

*Number of leaves.*—Approximately 30 to 35.

Inflorescence:

*Habit.*—Spike, dome-shaped, approximately 20–25 cm in diameter and 55–60 cm long, approximately 25 secondary spikes sprirally arranged on the main stem.

*Main stem.*—Round, downy, approximately 38–40 cm long and 1.5 cm in diameter, green-white in color, approximately RHS 157A.

*Primary bracts.*—Reaching up to one-half of the inflorescence, creamy white in color, RHS 159A, downy with pink, 51D. Abaxial is slightly darker than the adaxial; upper surface texture glabrous, lower surface texture tomentose, margins entire, elliptic shape, acute to attenuate apex, approximately 12 cm long and 4 cm wide.

*Secondary stem.*—Oval to flattened, approximately 0.8 long and 0.4 cm wide, 0.3 cm thick, downy, upper surface color RHS 39A over lay with grey RHS 191C, lower surface RHS 160B over lay with grey RHS 191C.

*Secondary bracts.*—Approximately 25 to 30 in number, reddish-pink, RHS 51D; upper surface texture glabrous, lower surface texture tomentose, margins entire, elliptic shape, acute to attenuate apex, approximately 5–9 cm long and 1–2 cm wide.

*Flower bracts.*—Upper surface texture glabrous, lower surface texture tomentose, margins entire, ovate to elliptic shape, acuminate apex, approximately 1–3 cm long and 1–2 cm wide, color RHS 51D.

*Flowers.*—1 per bract, many flowering at the same time.

*Petals.*—3, white to cream, upper and lower surface texture glabrous, margins entire, ovate to elliptic shape, acute to acuminate apex, approximately 7–10 mm long and 3–4 mm wide.

*Sepals.*—3, white RHS 158A, upper and lower surface texture glabrous, margins entire, ovate to elliptic shape, acute to acuminate apex, approximately 8–13 mm long and 3–6 mm wide.

*Stamens.*—6 per flower, white, approximately 5–10 mm long.

*Pistils.*—1 per flower with 3 lobed stigma, creamy white, approximately 8–10 mm long.

Other significant characteristics: The petals become less visible after the anthesis. The inflorescence holds its color for approximately 5 to 6 months.

I claim:

1. A new and distinct Aechmea plant named 'Maya', substantially as illustrated and described herein.

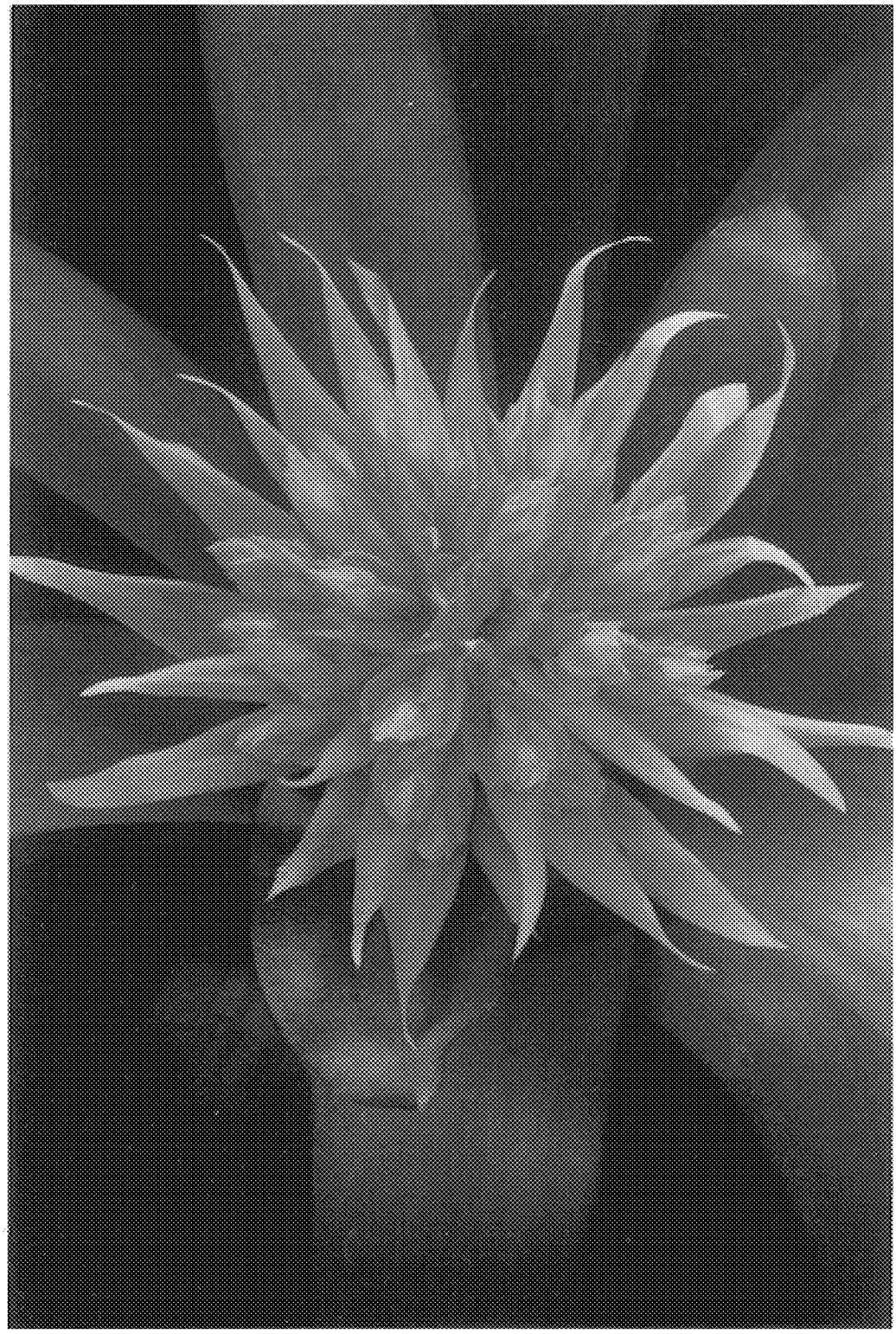

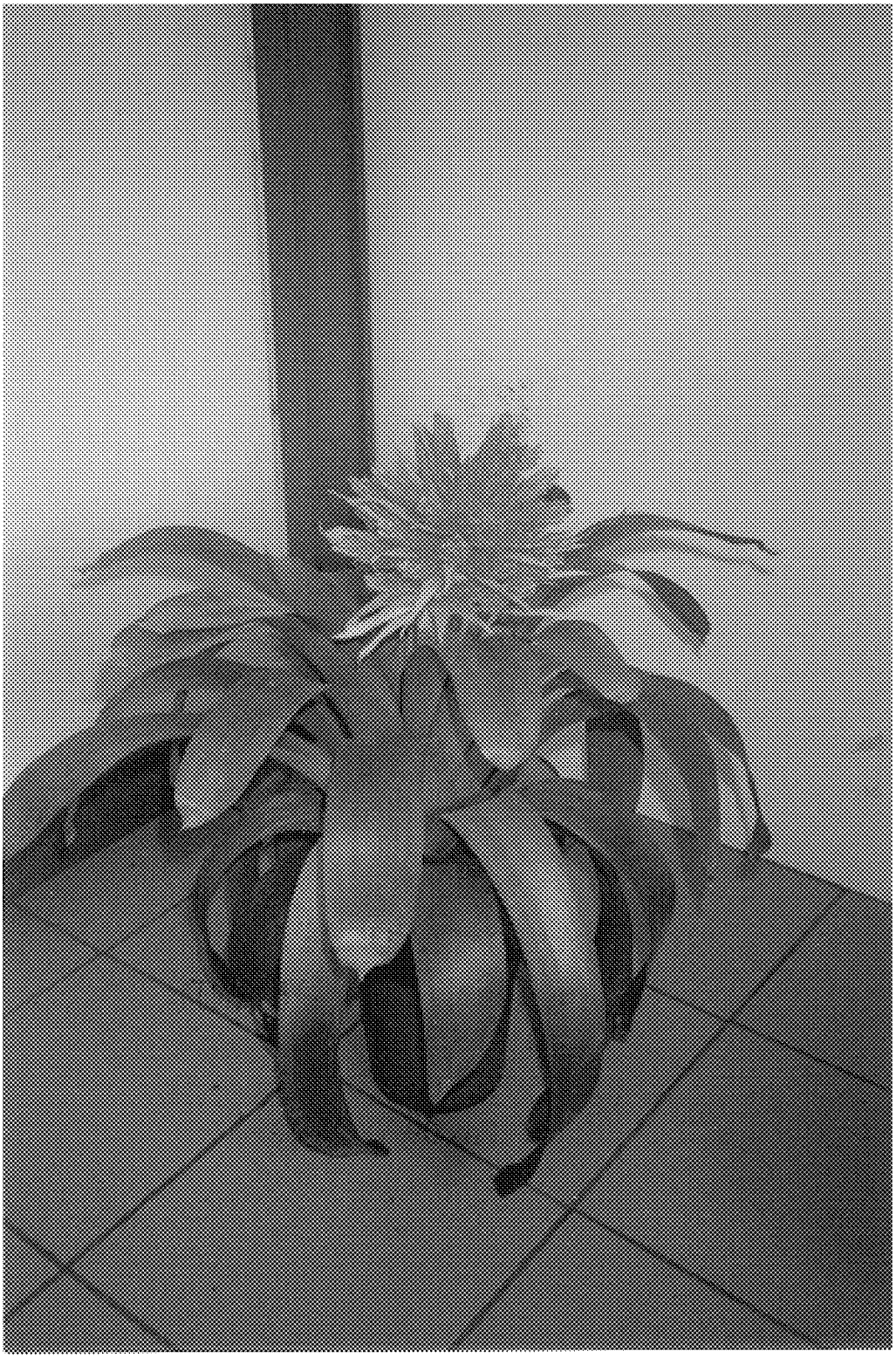

* * * * *